United States Patent [19]
Clements

[11] Patent Number: 5,925,032
[45] Date of Patent: Jul. 20, 1999

[54] SYRINGE CANNULA HOLDER

[75] Inventor: Don A. Clements, Arlington, Tex.

[73] Assignee: Alcon Laboratories, Inc., Fort Worth, Tex.

[21] Appl. No.: 09/024,854

[22] Filed: Feb. 17, 1998

[51] Int. Cl.$^6$ .................................................. A61B 17/00
[52] U.S. Cl. .............................. 606/1; 606/108; 604/192; 604/198; 604/263
[58] Field of Search ........................ 606/1, 108; 604/192, 604/198, 110, 263, 117, 197, 241

[56] References Cited

U.S. PATENT DOCUMENTS

| | | |
|---|---|---|
| 609,982 | 8/1898 | Winchester . |
| 1,012,700 | 12/1911 | Payne . |
| 1,157,552 | 10/1915 | Kispert . |
| 2,020,111 | 11/1935 | Eisele . |
| 2,806,473 | 9/1957 | Lingley . |
| 3,076,455 | 2/1963 | McConnaughey et al. . |
| 3,583,399 | 6/1971 | Ritsky . |
| 3,811,441 | 5/1974 | Sarnoff . |
| 3,895,633 | 7/1975 | Bartner et al. . |
| 4,112,945 | 9/1978 | Helixon et al. . |
| 4,122,836 | 10/1978 | Burnett . |
| 4,178,810 | 12/1979 | Takahashi ............................ 74/501 R |
| 4,540,405 | 9/1985 | Miller et al . |
| 4,592,746 | 6/1986 | Ewalt et al. . |
| 4,610,672 | 9/1986 | Burkholder et al. . |
| 4,994,045 | 2/1991 | Ranford . |
| 5,312,368 | 5/1994 | Haynes .................................. 604/192 |
| 5,356,395 | 10/1994 | Chen ..................................... 604/293 |
| 5,419,775 | 5/1995 | Haffner et al. . |
| 5,540,666 | 7/1996 | Barta et al. ............................ 604/192 |

Primary Examiner—John J. Wilson
Assistant Examiner—Pedro Philogene
Attorney, Agent, or Firm—Jeffrey S. Schira

[57] ABSTRACT

A syringe cannula holder having a split outer sleeve that can be folded around the cannula so as to engulf fully the cannula. The sleeve is held in place by a sliding retaining nut. A hinged, locking retainer holds the syringe within the sleeve.

6 Claims, 6 Drawing Sheets

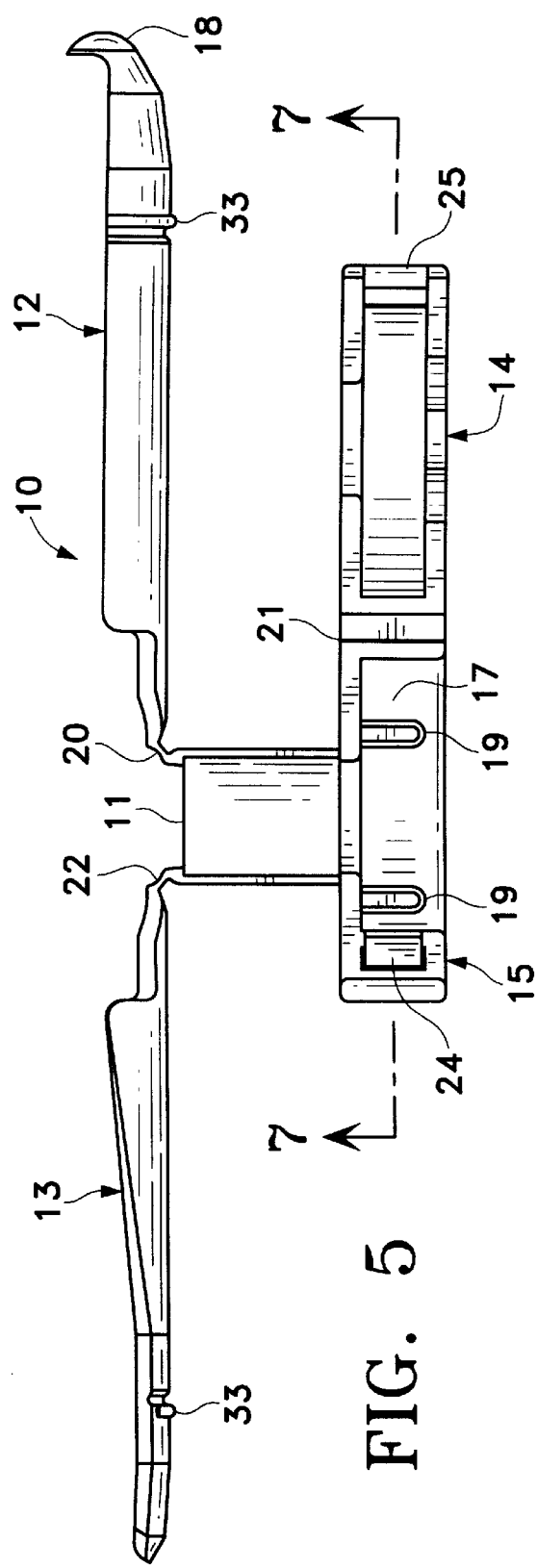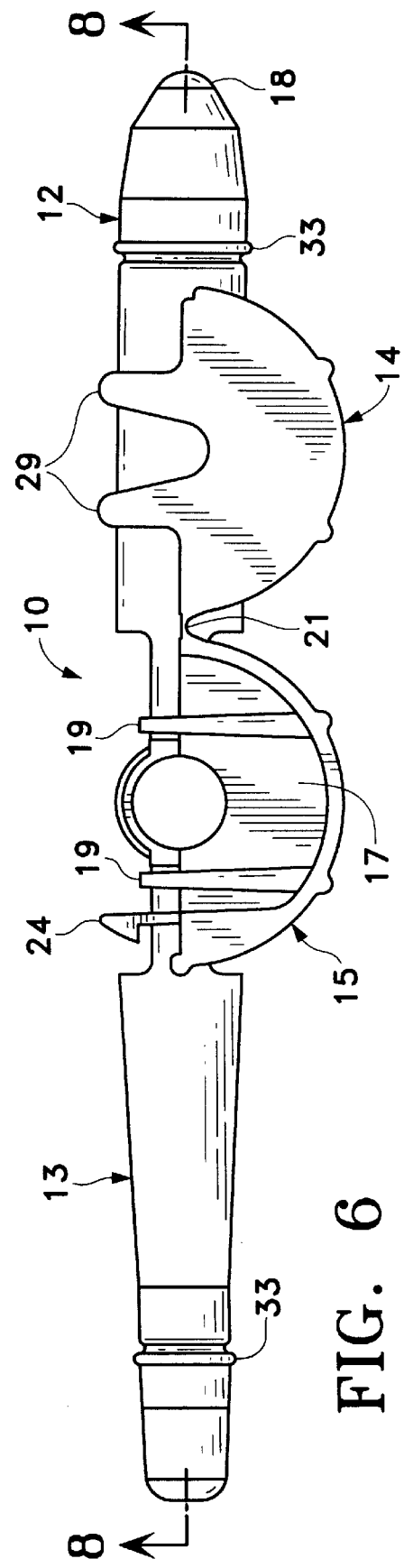

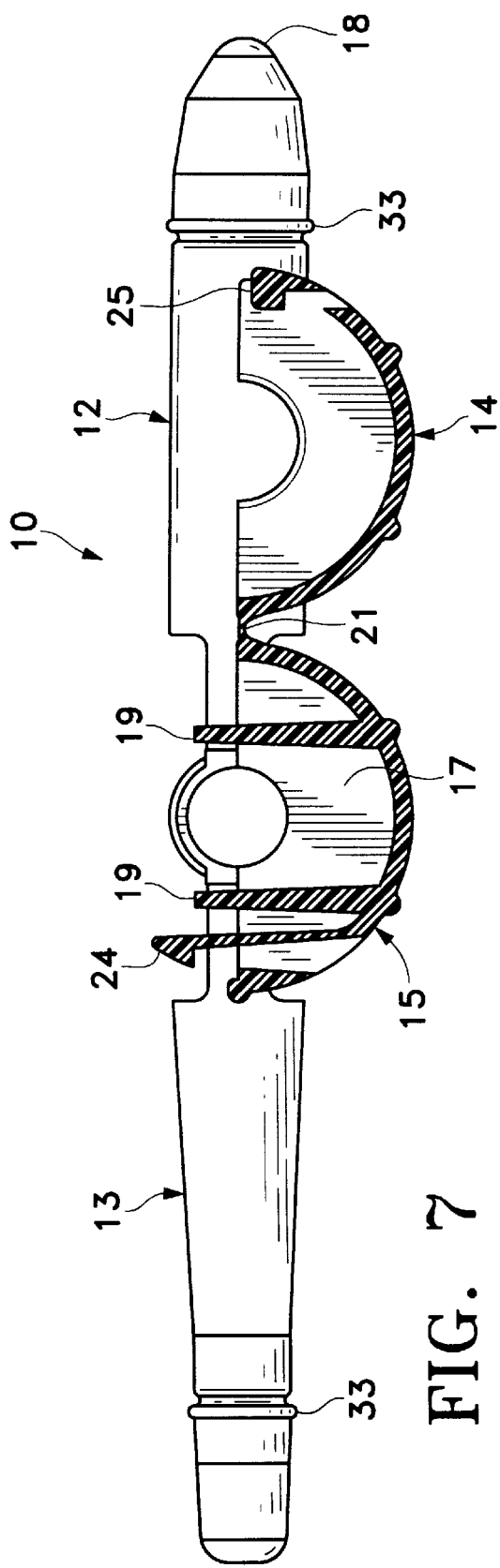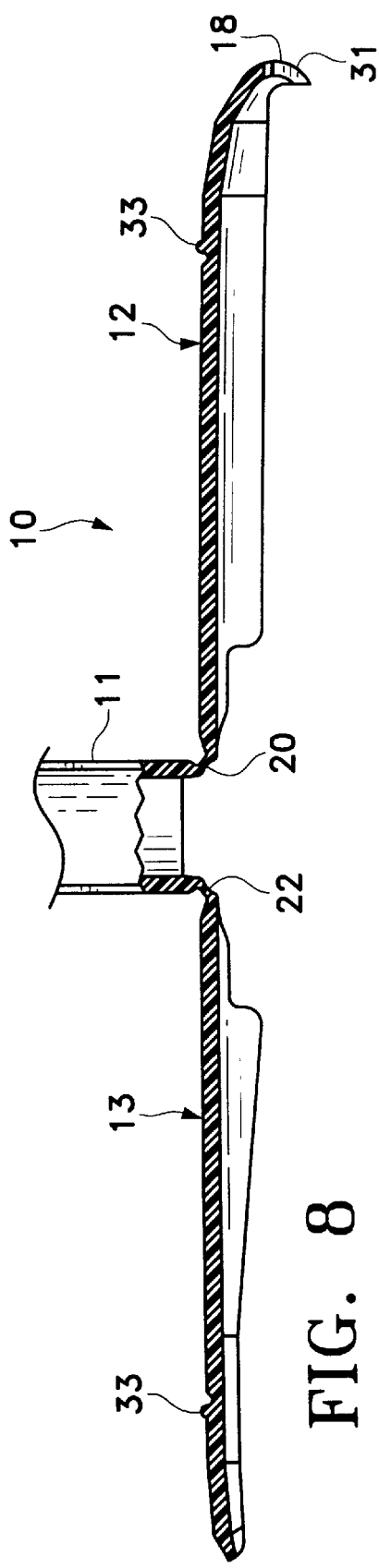

SYRINGE CANNULA HOLDER

BACKGROUND OF THE INVENTION

This invention relates generally to the field of syringes and, more particularly, to syringes used with viscoelastic agents.

During surgery, particularly ophthalmic surgery, various viscoelastic agents may be introduced into the surgical site. These agents generally are expressed into the surgical site out of a syringe and through a relatively thin cannula. The pressure at the syringe/cannula fitting can be very high due to the high viscosity of the viscoelastic agents. As a result, attempts to express the agent out of the cannula can cause the cannula to become disconnected from the syringe.

Prior art syringes intended for use with viscoelastic agents, such as described in U.S. Pat. No. 4,540,405 (Miller, et al.) have been directed primarily at providing a better grip on the relatively small syringe so that sufficient force can be applied to express the viscoelastic agent, and the cannula may still become disconnected from the syringe.

Accordingly, a need continues to exist for a holder that tightly secures a cannula on the end of a syringe.

BRIEF SUMMARY OF THE INVENTION

The present invention improves upon the prior art syringe and/or cannula holders by providing a holder having a split outer sleeve that can be folded around the cannula so as to engulf fully the cannula. The sleeve is held in place around the syringe by a sliding retaining nut. A hinged, locking retainer holds the syringe within the sleeve.

Accordingly, one objective of the present invention is to provide a cannula holder that helps to prevent the cannula from disconnecting from the syringe during use.

Another objective of the present invention is to provide a syringe sleeve having a split outer sleeve that may be folded to surround the syringe.

These and other advantages and objectives of the present invention will become apparent from the detailed description and claims that follow.

BRIEF DESCRIPTION OF THE DRAWINGS

FIG. 5 is a top plan view of the cannula holder of the present invention.

FIG. 6 is a front elevational view of the cannula holder of the present invention.

FIG. 7 is a cross-sectional view of the retaining ring that may be used with the present invention taken along line 7—7 in FIG. 5.

FIG. 8 is a cross-sectional view of the split sleeve that may be used with the present invention taken along line 8—8 in FIG. 6.

DETAILED DESCRIPTION OF THE INVENTION

Figure 1:
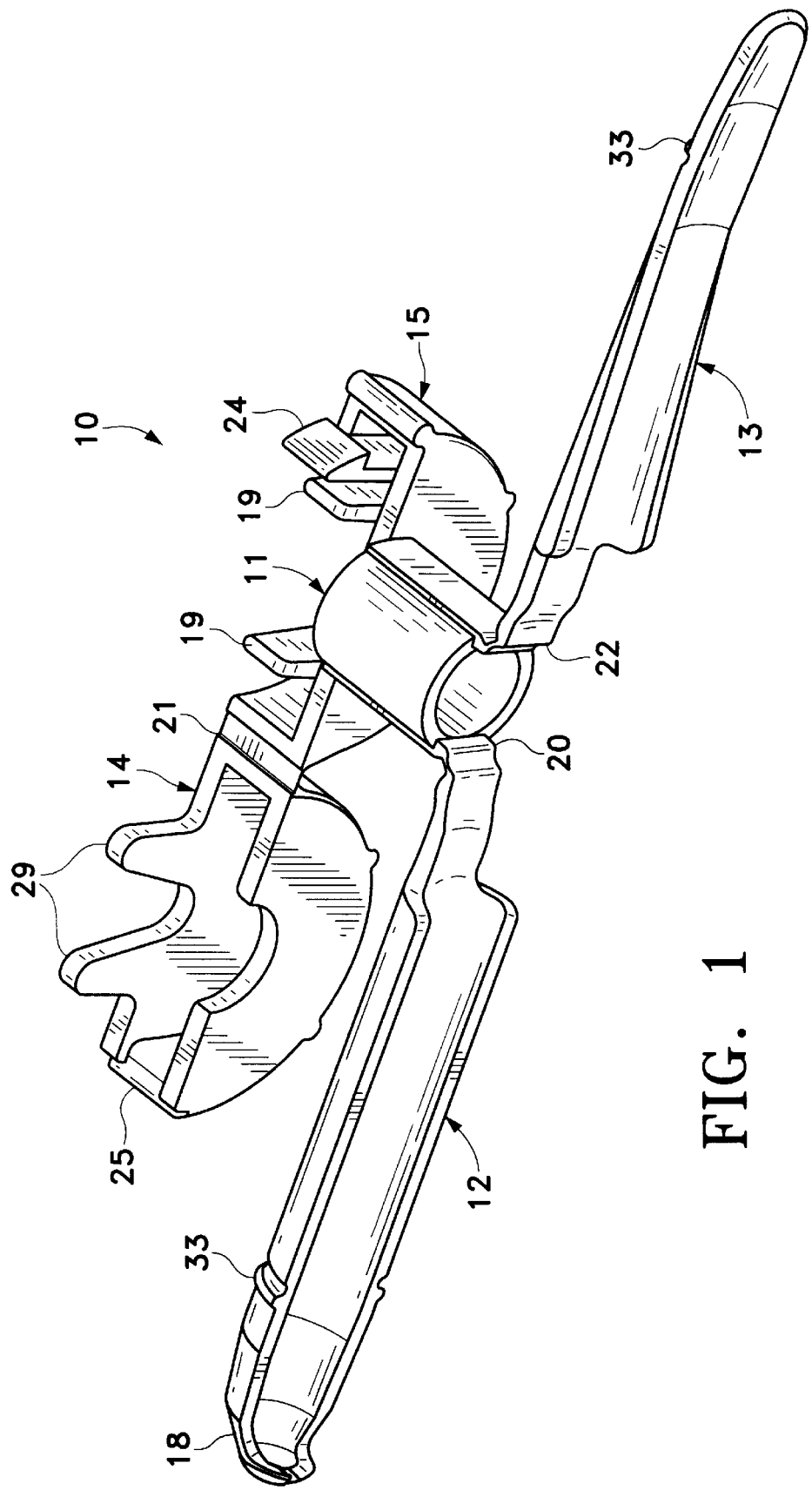
FIG. 1 is a perspective view of the cannula holder of the present invention shown unfolded.
Figure 2:
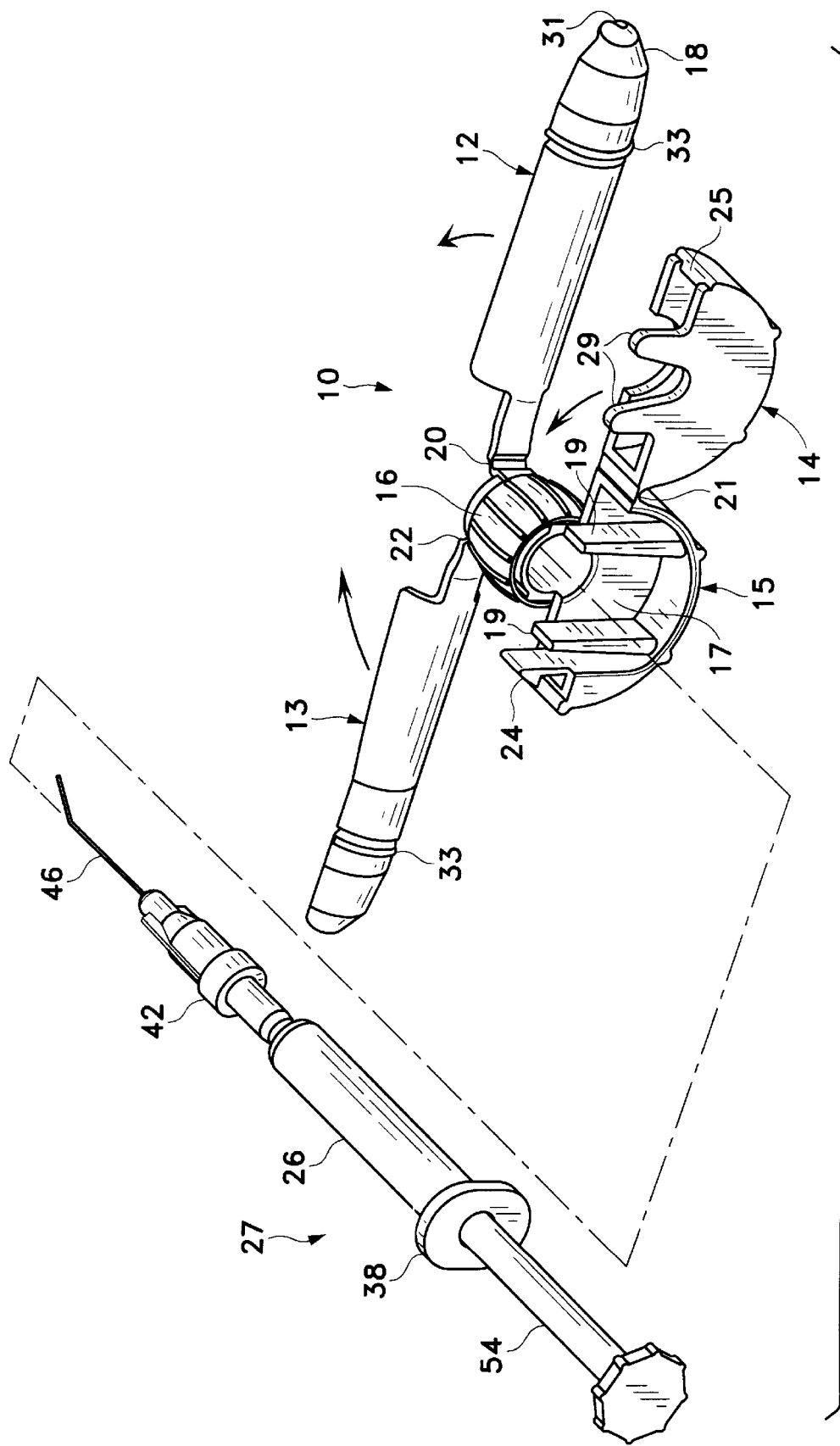
FIG. 2 is an expanded perspective view of the cannula holder of the present invention receiving a syringe and cannula.

As best seen in FIGS. 1 and 2, syringe cannula holder 10 of the present invention generally consists of barrel 11, split outer sleeve halves 12 and 13, split syringe retainer ring halves 14 and 15 and retaining nut 16. Split outer sleeve halves 12 and 13 are generally semi-tubular and sleeve half 12 contains cupped, slotted distal end 18. Sleeve halves 12 and 13 are connected on the proximal end to barrel 11 by hinges 20 and 22. Sleeve halves 12 and 13 may be sized and shaped to accept any commercially available syringe 26. Holder 10, including barrel 11, split outer sleeve halves 12 and 13 and split syringe retainer ring halves 14 and 15, is preferably molded as a single piece and may be made of any suitable material, such as plastic, with polycarbonate being preferred. Retaining nut 16 is molded as a separate piece from any suitable material, such as plastic, with polycarbonate being preferred, and is initially positioned over barrel 11 when sleeve halves 12 and 13 are in the open position.

Figure 3:
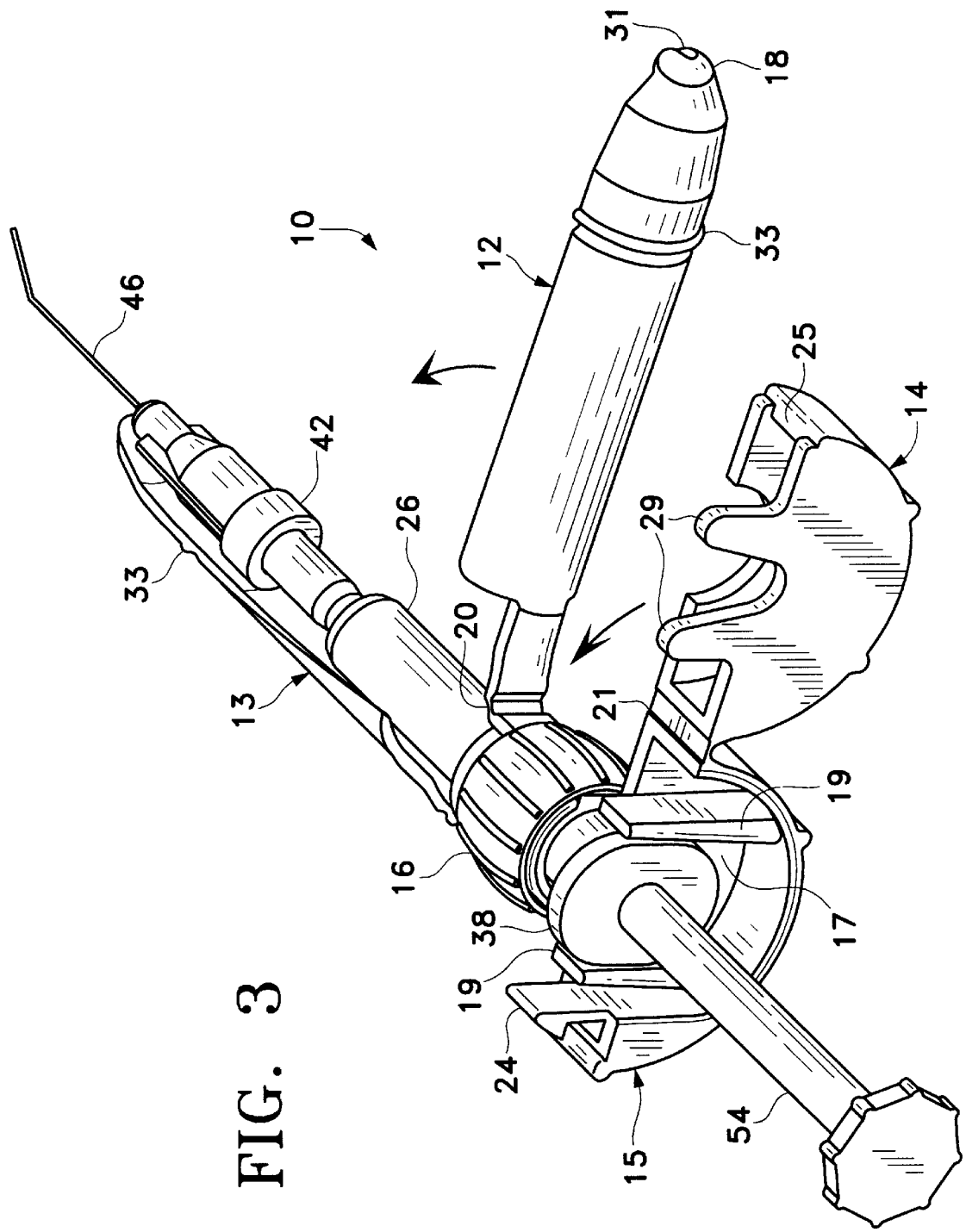
FIG. 3 is a perspective view of the cannula holder of the present invention shown being folded about the syringe.
Figure 4:
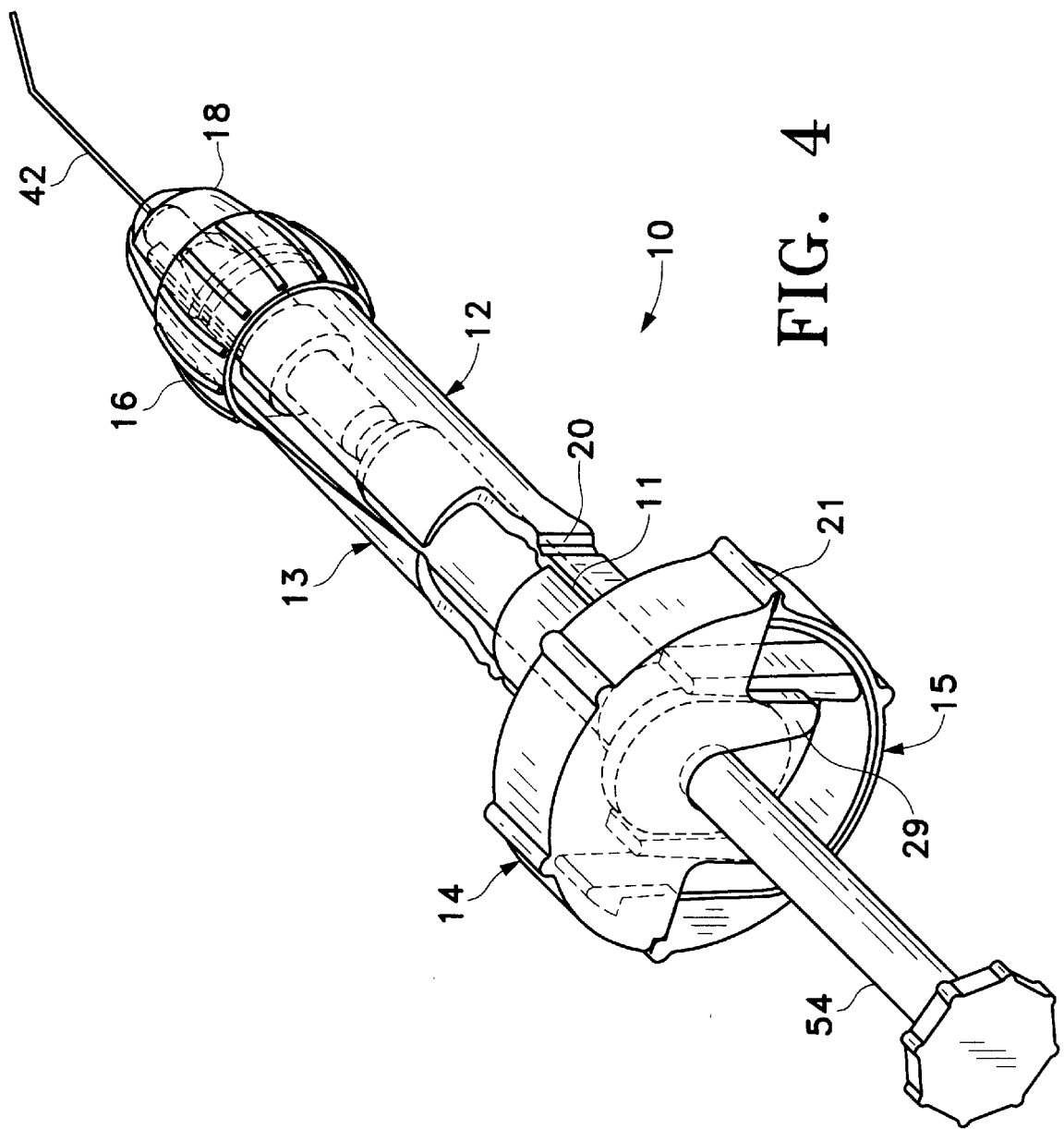
FIG. 4 is a perspective view of the cannula holder of the present invention with the syringe shown in shadow line.

As best seen in FIGS. 2, 3 and 4, in use, plunger 54 is inserted into syringe 26 and plunger/syringe assembly 27 is inserted through barrel 11 so that it is held between open sleeve halves 12 and 13. Flange 38 on syringe 26 fits within recess 17 in retaining ring half 15 and centered in place by fingers 19. Retainer half 14 is pivoted about hinge 21 until snap 24 on retainer half 15 engages catch 25 on retainer half 14. As best seen in FIG. 4, flange 38 is prevented from sliding out of recess 17 by projections 29 on retainer half 14. Cannula assembly 42 is inserted onto syringe 26 and sleeve halves 12 and 13 are pivoted about hinges 20 and 22 so that sleeve halves 12 and 13 fit snugly against opposite sides of syringe 26 and cannula assembly 42 and slot 31 on end 18 of sleeve half 12 slides over cannula 46 on cannula assembly 42. Retaining nut 16 is slid from over barrel 11 down the length of sleeve halves 12 and 13 toward end 18, as best seen in FIG. 4, and held in place by at distal end 18 by frictional contact with ridge 33.

This description is given for purposes of illustration and explanation. It will be apparent to those skilled in the relevant art that modifications may be made to the invention as herein described without departing from its scope or spirit.

I claim:

1. A cannula holder for a syringe, comprising:
   a) a barrel having a pair of split, retainer ring halves on one end;
   b) a pair of semi-tubular outer sleeve halves connected on a proximal end by hinges to the barrel opposite the retainer ring halves; and
   c) a retaining nut sized to fit over the barrel and the outer sleeve halves when the outer sleeve halves are pivoted together about the hinges.

2. The cannula holder of claim 1 wherein the barrel, retainer ring halves and outer sleeve halves are integrally molded plastic.

3. The cannula holder of claim 1 wherein the syringe has a flange and the retainer ring halves contain a means for retaining the flange within a recess in the retainer ring halves.

4. The cannula holder of claim 1 wherein the outer sleeve halves contain a ridge for frictionally holding the retaining nut at the distal end of the outer sleeve halves.

5. A cannula holder for a syringe, the syringe having a flange, comprising:
   a) a barrel having a pair of split, retainer ring halves on one end;
   b) a pair of semi-tubular outer sleeve halves having a ridge on a distal end connected on a proximal end by hinges to the barrel opposite the retainer ring halves;
   c) means for retaining the flange within a recess in the retainer ring halves; and d) a retaining nut sized to fit over the barrel and the outer sleeve halves when the outer sleeve halves are pivoted together about the hinges.

6. The cannula holder of claim 5 wherein the barrel, retainer ring halves and outer sleeve halves are integrally molded plastic.

* * * * *